United States Patent [19]

Jacobson et al.

[11] Patent Number: 5,015,652
[45] Date of Patent: May 14, 1991

[54] 1-DIMETHYLCARBAMOYL-3-SUBSTITUTED-5-SUBSTITUTED-1H-1,2,4-TRIAZOLES

[75] Inventors: Richard M. Jacobson, Chalfont; Luong T. Nguyen, Lansdale, both of Pa.

[73] Assignee: Rohm and Haas Company, Philadelphia, Pa.

[21] Appl. No.: 176,919

[22] Filed: Apr. 4, 1988

[51] Int. Cl.$^5$ .................. C07D 249/12; A01N 43/653
[52] U.S. Cl. ................................. 514/384; 548/264.4
[58] Field of Search ............... 548/265, 269, 264.4; 514/384

[56] References Cited

U.S. PATENT DOCUMENTS

| | | |
|---|---|---|
| 3,308,131 | 3/1967 | McKusick ............................ 548/265 |
| 3,973,028 | 8/1976 | Doyle Jr. et al. ................... 548/265 |
| 4,038,387 | 7/1977 | Doyle, Jr. et al. .................. 548/265 |
| 4,054,664 | 10/1977 | Watkins et al. ..................... 548/265 |
| 4,066,774 | 1/1978 | Kirkpatrick ........................ 548/265 |
| 4,160,839 | 7/1979 | Kirkpatrick ........................ 548/265 |
| 4,220,790 | 9/1980 | Kirkpatrick ........................ 548/265 |
| 4,255,435 | 3/1981 | Watkins et al. ..................... 548/265 |
| 4,291,043 | 9/1981 | Kristiansen et al. ................ 548/265 |
| 4,742,060 | 5/1988 | Shiokawa et al. ................... 514/383 |
| 4,742,072 | 5/1988 | Jacobson ........................... 548/265 |

FOREIGN PATENT DOCUMENTS

| | | |
|---|---|---|
| 0029407 | 5/1981 | European Pat. Off. ............ 548/265 |
| 0213718 | 11/1987 | European Pat. Off. ............ 548/265 |
| 2412564 | 10/1974 | Fed. Rep. of Germany ...... 548/265 |
| 3021232 | 12/1980 | Fed. Rep. of Germany ...... 548/265 |
| 3031191 | 3/1981 | Fed. Rep. of Germany ...... 548/265 |

OTHER PUBLICATIONS

Gupta, A. and Misra, H., "Synthesis and Pesticidal Activities of Some New Substituted 1,2,4-Triazoles and Their Derivatives", *Agric. Biol. Chem.*, 44, pp. 1009-1013 (1980).

McCalley, N., "Cabbage Aphid Control on Brussel Sprouts and Broccoli" *California Agriculture*, pp. 7-8 (1982).

*Primary Examiner*—Richard E. Raymond
*Assistant Examiner*—Mark W. Russell
*Attorney, Agent, or Firm*—Barbara V. Maurer

[57] ABSTRACT

This invention relates to 1-dimethylcarbamoyl-3-substituted-5-substituted-1H-1,2,4-triazoles having the formula

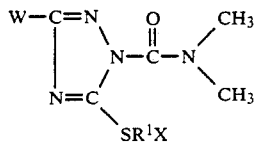

wherein $R^1$, W and X are as defined herein, compositions containing these compounds and methods of use as insecticides.

25 Claims, No Drawings

1-DIMETHYLCARBAMOYL-3-SUBSTITUTED-5-SUBSTITUTED-1H-1,2,4-TRIAZOLES

BACKGROUND OF THE INVENTION

This invention relates to novel 1-dimethylcarbamoyl-3-substituted-5-substituted-1H-1,2,4-triazoles which are useful as insecticides, compositions containing those compounds and methods of use.

Certain 1,2,4-triazoles have been disclosed as having pesticidal activity.

U.S. Pat. No. 3,308,131 describes a group of 1,2,4-triazoles having the general formula $$R^4-C\underset{\underset{\underset{R^1}{N}}{\underset{|}{C=X}}}{\overset{\overset{N\text{———}C-R^3}{\|}}{\|}}\text{N} \quad \text{and} \quad R^4-C\underset{N}{\overset{N=C-R^3}{\underset{\|}{|}}}N-\underset{X}{\overset{\|}{C}}-N\underset{R^2}{\overset{R^1}{\diagdown}}$$

where X is oxygen or sulfur, $R^1$ and $R^2$ are aliphatic groups containing up to 14 carbons and which may be joined to form a heterocyclic ring with the carbamoyl nitrogen atom and $R^3$ and $R^4$, which together contain up to 14 carbon atoms, are free from aliphatic unsaturation and are selected from hydrogen, halogen, sulfonyl, mercapto, cyano, hydrocarbyl, halohydrocarbyl, nitrohydrocarbyl, hydroxycarbyloxycarbonylhydrocarbyl, hydrocarbylsulfonyl, hydrocarbylmercapto, nitrohydrocarbylmercapto, halohydrocarbylmercapto, aminohydrocarbylmercapto and hydrocarbyloxyhydrocarbyl. These compounds are disclosed to be useful as insecticides, in dyeing textiles and as analgesics.

U.S. Pat. No. 4,291,043 disloses 1-N,N-dimethylcarbamoyl-3(5)-alkyl-5(3)-alkylthioalkylthio-1,2,4-triazoles having insecticidal activity. The 3(5) substituents include i-propyl, s-butyl, t-butyl or optionally methyl-substituted cyclopropyl and a group having the formula $$-S-CH(R')-(CH_2)_n-S-R''$$

where R' is H or methyl, R'' is lower $(C_1-C_4)$alkyl and n is 0 or 1.

U.S. Pat. Nos. 3,973,028 and 4,038,387 disclose 1-dimethylcarbamoyl-3-branched alkyl-1,2,4-triazol-5-yl-(N-substituted)sulfonamides having insecticidal activity. The branched alkyl groups include $C_3$ to $C_4$ secondary or tertiary alkyl and cycloalkyl.

U.S. Pat. No. 4,054,664 discloses 1(2)-(N,N-disubstituted carbamoyl)-3,5-substituted-1,2,4-triazoles having insecticidal activity. The 3(5) substituents include i-propyl, s-butyl, t-butyl and S—R where R is methyl, ethyl, propyl, vinyl, prop-2-ynyl, but-2-enyl or 2-haloalkyl.

U.S. Pat. No. 4,255,435 discloses 1(2)-N,N-disubstituted carbamoyl)-3,5-substituted-1,2,4-triazoles having activity against a variety of economically important insects and nematodes. The 3(5) substituents include isopropyl, s-butyl, t-butyl, The 5(3)substituents include S—R where R is methyl, ethyl, propyl, vinyl, 2-propynyl, 2-butenyl and 2-haloallyl.

U.S. Pat. No. 4,160,839 discloses 1-N,N-dimethylcarbamoyl-3,5-substituted-1,2,4-triazoles having insecticidal activity. The 3-substituents include t-butyl, propyl, cyclopropyl, isopropyl or 1-methylpropyl. The 5-substituents include S-R where R is 2-propynyl, allyl, 2-bromoallyl, 2-chloroallyl, 2-methylallyl, 1-methylallyl or 2,3,3-trichloroallyl.

U.S. Pat. Nos. 4,220,790 and 4,066,774 disclose 1-N,N-dimethylcarbamoyl-3-tert-butyl-5-methylthio-1,2,4-triazole having insecticidal activity and a method of killing insects using said triazole.

DE 3031191A1 discloses 1-dimethylcarbamoyl-3(or 5)-benzylthio-5(or 3)-alkyl-1,2,4-triazoles having insecticidal activity. The 5(or 3) substituents include isopropyl, s-butyl, t-butyl or optionally methyl substituted cyclopropyl.

DE 3021232 discloses 1-dimethylcarbamoyl-1,2,4-triazoles having insecticidal activity. The 3(or 5) position is substituted with the group $$-\underset{R^2}{\underset{|}{\text{SCH}}}-(CH_2)_n-SR^1$$

wherein $R^1$ is $(C_1-C_4)$alkyl, $R^2$ is hydrogen or methyl and n is 0 or 1.

EP 0,029,407 discloses 1-N,N'-dimethylcarbamoyl-3,5-substituted-1,2,4-triazoles having insecticidal activity. The 3-substituents include i-propyl, s-butyl, t-butyl or cyclopropyl. The 5-substituents include $S(CH_2)_nOR^2$ where $R^2$ is $(C_1-C_3)$alkyl and n is 1 or 2.

The present invention discloses 1-dimethylcarbamoyl-3-substituted-5-substituted-1H-1,2,4-triazoles. These compounds are distinguished primarily by their novel 5-position substituents.

Compounds of the present invention are also distinguished by their insecticidal activity against sucking insects such as those of the order Homoptera and especially those of the family Aphididae.

Accordingly, compounds of the present invention are particularly suitable for controlling plant-destructive insects in crops of cultivated plants and ornamentals, especially in crops of fruit and vegetables.

It is therefore an objective of the present invention to provide novel compounds, and compositions containing said compounds, which possess insecticidal activity. It is a further object of this invention to provide methods for controlling insects using the novel compounds.

SUMMARY OF THE INVENTION

In accordance with the present invention, there are provided compounds having the formula $$\underset{\underset{SR^1X}{\diagup}}{\overset{W-C=N}{\underset{N=C}{\big|}}}\overset{\diagdown}{\underset{\diagup}{N}}-\overset{\overset{O}{\|}}{C}-N\underset{CH_3}{\overset{CH_3}{\diagdown}} \qquad I$$

wherein

W is t-butyl, s-butyl, i-propyl, cyclopropyl, 1-methylthio-1-methylethyl or 1-methylcycloprop-1-yl;

X is $$-\underset{R^3}{\underset{|}{N}}COR^2, \quad -OCOR^2 \quad \text{or} \quad -\underset{R^3}{\underset{|}{N}}CSR^2;$$

$R^1$ is unsubstituted or substituted $-(CH_2)_n-$ having one to four of the same or different substituents independently selected from halo, cyano, nitro, —OR, —CO$_2$R, —OCOR, —COR, (C$_2$-C$_6$)alkenyl, (C$_2$-C$_6$)alkynyl, (C$_1$-C$_6$)alkyl, (C$_1$-C$_6$)haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$)alkoxy, (C$_1$-C$_4$)haloalkyl or (C$_2$-C$_6$)alkenyl;

each R$^2$ is independently hydrogen; unsubstituted or substituted (C$_1$-C$_8$)alkyl having one to three of the same or different substituents independently selected from halo, cyano, amino, nitro, —OR, —CO$_2$R, —COR or —OCOR; unsubstituted or substituted (C$_1$-C$_8$)alkoxy having one to three of the same or different substituents independently selected from halo, cyano, nitro, —OR, —CO$_2$R, —COR or —OCOR; unsubstituted or substituted (C$_1$-C$_{12}$)mono- or dialkylamino where the alkyl is substituted by one to three of the same or different substituents independently selected from halo, cyano, nitro, —OR, —CO$_2$R, unsubstituted or substituted (C$_6$-C$_{14}$)arylamino where the aryl is substituted by one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$)alkoxy, (C$_1$-C$_4$)-haloalkyl or (C$_2$-C$_6$)-alkenyl; unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$) alkoxy, (C$_1$-C$_4$)-haloalkyl or (C$_2$-C$_6$)alkenyl;

R$^3$ is hydrogen; unsubstituted or substituted (C$_1$-C$_6$)alkyl having from one to four of the same or different substituents independently selected from halo, cyano, nitro, —OR, —CO$_2$R, —OCOR, —COR, (C$_2$-C$_6$)alkenyl, (C$_2$-C$_6$)alkynyl, (C$_1$-C$_6$)alkyl, (C$_1$-C$_6$)haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$)alkoxy, (C$_1$-C$_4$)haloalkyl or (C$_2$-C$_6$)-alkenyl;

where each R is independently hydrogen; (C$_1$-C$_6$)alkyl; or phenyl optionally substituted with one to three of the same or different substituents independently selected from halo, cyano, nitro, hydroxy, trifluoromethoxy, difluoromethoxy, tetrafluoroethoxy, trifluoromethylthio, tetrafluoroethylthio, (C$_1$-C$_4$)alkyl, (C$_1$-C$_4$)alkoxy, (C$_1$-C$_4$)haloalkyl, (C$_2$-C$_6$)alkenyl, carboxy, (C$_1$-C$_4$)alkoxycarbonyl;

n is 1 to 10; and agronomically acceptable salts thereof.

Further, in accordance with the present invention, there are provided compositions containing compounds of the present invention and methods of using said compounds and compositions.

DETAILED DESCRIPTION OF THE INVENTION

The term "halo" includes fluoro, chloro, bromo and iodo.

The term "alkyl" should be understood as including straight or branched chain moieties such as methyl, ethyl, n-propyl, isopropyl, n-butyl, t-butyl, isobutyl, neopentyl, isooctyl and the like.

The term haloalkyl is an alkyl group having the stated number of carbon atoms having one or more of the same or different halo toms bonded thereto such as bromomethyl, dichloromethyl, trifluoromethyl, fluorochloromethyl, tetrafluoroethyl and the like.

In a preferred embodiment, compounds of the invention include those of Formula I where W is t-butyl;

X is —NHCOR$^2$, —OCOR$^2$ or —NHCSR$^2$,

R$^1$ is —(CH$_2$)$_n$—,

R$^2$ is unsubstituted or substituted (C$_1$-C$_8$)alkyl; unsubstituted or substituted (C$_1$-C$_8$)alkoxy; unsubstituted or substituted mono(C$_1$-C$_8$)-alkylamino; unsubstituted or substituted di(C$_1$-C$_4$)alkylamino; unsubstituted or substituted phenylamino; where the substituent is from one to two groups independently selected from halo, (C$_1$-C$_4$)haloalkyl, (C$_1$-C$_4$)alkoxy or (C$_1$-C$_4$)thioalkoxy;

R$^3$ is hydrogen; and n is 2 or 3; and agronomically acceptable salts thereof.

More preferred compounds of the invention include those of Formula I where

W is t-butyl;

X is —NHCOR$^2$, —OCOR$^2$ or —NHCSR$^2$;

R$^1$ is —(CH$_2$)$_n$—;

R$_2$ is (C$_1$-C$_8$)alkyl, (C$_1$-C$_8$)haloalkyl; (C$_1$-C$_8$)-alkoxy; (C$_1$-C$_8$)monoalkylamino; (C$_1$-C$_8$)-dialkylamino; phenyl; phenylamino; halophenylamino; halo-substituted alkylphenylamino; and n is 2 or 3; and agronomically acceptable salts thereof.

Most preferred compounds of the invention include those of Formula I where

W is t-butyl;

R$^1$ is —(CH$_2$)$_2$—; and

X is NHCO$_2$CH$_3$, NHCON(CH$_3$)$_2$ or NHCOCH$_3$.

Since the 1-dimethylcarbamoyl-3-substituted-5-substituted-1H-1,2,4-triazoles of Formula I may possess acidic or basic functional groups, they may form novel salts with appropriate bases or acids which also exhibit insecticidal activity.

Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. Among the ammonium salts are those in which the ammonium cation has the formula NR$^9$R$^{10}$R$^{11}$R$^{12}$ wherein each of R$^9$, R$^{10}$, Rll and R$^{12}$ are independently a hydrogen atom, a hydroxy group, a (C$_1$-C$_4$)alkoxy group, a (C$_1$-C$_{20}$)alkyl group, a (C$_2$-C$_8$)hydroxyalkyl alkenyl group, a (C$_3$-C$_8$)alkyl group, a (C$_2$-C$_8$)hydroxyalkyl group, a (C$_2$-C$_8$)alkoxyalkyl group, a (C$_2$-C$_6$)-alkylamino group, a (C$_2$-C$_6$)haloalkyl group, an amino group, a (C$_1$-C$_4$)alkyl or (C$_1$-C$_4$)dialkylamino group, a substituted or unsubstituted phenyl group, a substituted or unsubstituted phenylalkyl group, having up to four carbon atoms in the alkyl moiety, or any two of R$^9$, R$^{10}$, R$^{11}$ or R$^{12}$ can be taken together to form with the nitrogen atom a 5- or 6-membered heterocyclic ring, optionally having up to one additional hetero atom (e.g., oxygen, nitrogen or sulfur) in the ring, and preferably saturated, such as piperidino, morpholino, pyrrolidino, piperazino or the like, or any three of $R^9$, $R^{10}$, $R^{11}$ or $R^{12}$ can be taken together to form with the nitrogen atom a 5- or 6-membered aromatic heterocyclic ring, such as piperazole or pyridine. When the ammonium group contains a substituted phenyl or substituted phenylalkyl group, the substituents will generally be selected from halogen atoms, $(C_1-C_8)$alkyl groups, $(C_1-C_4)$alkoxy groups, hydroxy groups, nitro groups, trifluoromethyl groups, cyano groups, amino groups, $(C_1-C_4)$alkylthio groups and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethyl ammonium, moroholinium, piperidinium, 2-phenethylammonium, 2-methylbenzylammonium, n-hexylammonium, triethylammonium, trimethylammonium, tri(n-butyl)ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium and the like.

Among the acid addition salts are those in which the anion is an agronomically acceptable anion such as chloride, bromide, sulfate, nitrate, perchlorate, acetate, oxalate or the like.

In a preferred embodiment, the agronomically acceptable salts include the sodium, potassium, ammonium, alkylammonium, chloride and sulfate salts.

The 1-dimethylcarbamoyl-3-substituted-5-substituted-1H-1,2,4-triazoles of the present invention or their precursors are prepared by alkylating the sulfur (S-alkylating) a 3-substituted-5-thio-1H-1,2,4-triazole in a solvent or diluent and optionally in the presence of an acid scavenger with a compound having the formula

Z—R$^1$—X to obtain 3-substituted-5-substituted-1H-1,2,4-triazoles having the formula

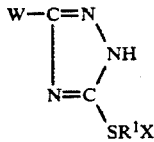
III where $R^1$ and X are as defined above for Formula I and Z is a good leaving group such as those described in "Basic Principles of Organic Chemistry" by Roberts and Caserio, W. A. Benjamin Inc., New York 1965, p. 290, incorporated herein by reference. Examples of leaving groups include halo (chloro, bromo or iodo), alkyl sulfonate, aryl sulfonate or alkyl sulfate.

Suitable solvents or diluents for the above process include those which are inert to the reactants, for example, methanol, ethanol, ethyl acetate, tetrahydrofuran, dimethylformamide or acetonitrile and the like.

Suitable acid scavengers for the above process, such as triethylamine or diisopropylethylamine may be added during alkylation or, if desired, the 3-substituted-5-thio-1H-1,2,4-triazole can be pretreated with an acid scavenger such as sodium hydride or sodium hydroxide.

Generally, equivalent molar amounts of starting materials in an overall concentration of from about 0.01 molar to about 5 molar are used, and the above process is carried out at from about 0° C. to about 150° C. for from about 5 minutes to about 2 days. Preferably the starting materials are present in a concentration of from about 0.1 molar to 1 molar and the reaction is carried out from about 20° C. to about 90° C.

Modifications to the above process may be necessary to accommodate reactive functionalities of particular 5-substituents. Such modifications would be apparent and known to those skilled in the art.

The 3-substituted-5-substituted-1H-1,2,4-triazole (III) obtained by the above process is then reacted with a compound having the formula

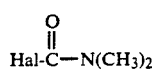
IV where Hal is halogen (chloro, bromo or iodo) in the presence of a suitable acid scavenger and optionally a suitable acylation catalyst.

Suitable acid scavengers for this process include tertiary amines such as triethylamine, diiscpropylamine pyridine and the like.

Suitable acylation catalysts include tertiary amines such as 4-dimethylaminopyridine, 4-pyrrolidinopyridine, triethylamine, pyridine and the like. Generally, when the acylation catalyst is used, it is present in the reaction mixture in an amount from about 0.001 to about 0.25 molar equivalent of the starting material.

In an embodiment of the invention, the 1-dimethylcarbamoyl-3-substituted-5-substituted-1H-1,2,4-triazoles are prepared by S-alkylating a 3-substituted-5-thio-1H-1,2,4-triazole, optionally in the presence of acid scavenger, with a compound having the formula

Z—R$^1$—Y where $R^1$ is as defined above, Z is a good leaving group as defined above such as halo (chloro, bromo or iodo), alkyl sulfonate, aryl sulfonate or alkyl sulfonate and Y is amino or hydroxy to obtain 3-substituted-5-(amincalkylthio) or (hydroxyalkylthio)-1H-1,2,4-triazoles having the formula

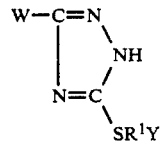
VI

Suitable solvents or diluents for the above process include those which are inert to the reactants such as methanol, ethanol, ethyl acetate, tetrahydrofuran, dimethylformamide, acetonitrile and the like.

The 3-substituted-5-(aminoalkylthio) or (hydroxyalkylthio)-1H-1,2,4-triazole (VI) obtained by the above process is then reacted with an isocyanate, acid chloride or isothiocyanate under conditions known to one skilled in the art to obtain the intermediate compounds of formula III.

Generally, equivalent molar amounts of starting materials in an overall concentration of from about 0.01 molar to about 5 molar are used, and the above process is carried out at from about 0° C. to about 150° C. for from about 5 minutes to about 2 days. Preferably the starting materials are present in a concentration of from about 0.1 molar to 1 molar and the reaction is carried out from about 20° C. to about 90° C..

The compounds of Formula II, IV and V can be prepared from known precursors by known methods.

The 3-substituted-5-thio-1H-1,2,4-triazoles used as a starting material can be prepared from known precursors by known methods as illustrated below for Example No. 1.

After preparing compounds embraced by Formula I by the above process, the salts of the invention can be prepared by any convenient art-recognized method, such as by reacting a metal hydroxide, a metal hydride or an amine or ammonium salt, such as a halide, hydroxide or alkoxide with the free acid, or reacting a quaternary ammonium salt, such as chloride, a bromide, nitrate or the like with a metal salt of the invention in a suitable solvent. When metal hydroxides are used as reagents, useful solvents include water, glyme, dioxane, tetrahydrofuran, methanol, ethanol, isopropanol and the like. When metal hydrides are used as reagents, useful solvents include nonhydroxylic solvents such as dioxane, glyme, tetrahydrofuran, diethyl ether, hydrocarbons such as toluene, xylene, hexane, pentane, heptane, octane, dimethylformamide and the like. When amines are used as reagents, useful solvents include alcohols, such as methanol or ethanol, hydrocarbons, such as toluene, xylene, hexane and the like, tetrahydrofuran, glyme, dioxane or water. When ammonium salts are used as reagents, useful solvents include water, alcohols, such as methanol or ethanol, glyme, tetrahydrofuran or the like. When the ammonium salt is other than a hydroxide or alkoxide, an additional base, such as potassium or sodium hydroxide, hydride or alkoxide is generally used. The particular choice of solvent will depend on the relative solubilities of the starting materials and the resultant salts, and slurries rather than solutions of certain reagents may be used to obtain the salts. Generally, equivalent amounts of the starting reagents are used and the salt-forming reaction is carried out at about 0° C. to about 100° C., preferably at about room temperature at atmospheric pressure.

The acid addition salts of the present invention can be prepared by any convenient art-recognized method such as by reacting hydrochloric, hydrobromic, sulfuric, nitric, phosphoric, acetic, propionic, benzoic or other suitable acid with a compound of the present invention having a basic functionality in a suitable solvent. Useful solvents include water, alcohols, ethers, esters, ketones, haloalkanes and the like. The particular choice of solvent will depend on the relative solubilities of the starting materials and the resulting salts and slurries rather than solutions of certain reagents may be used to obtain the salts. Generally, equivalent molar amounts of starting materials are used and the salt-forming reaction is carried out at from about −100° C. to about 100° C., preferably at about room temperature.

The following examples will further illustrate this invention but are not intended to limit it in any way. In Table I, representative examples of 1-dimethylcarbamoyl-3-substituted-5-substituted-1H-1,2,4-triazoles of the present invention are listed. Structures were confirmed by NMR and in some cases by IR and/or elemental analysis. Specific illustrative preparations of several of the compounds are described after Table I.

TABLE I $$\begin{array}{c} W-C=N \\ | \quad\quad\quad N-C(=O)-N(CH_3)_2 \\ N=C \\ | \\ SR^1X \end{array}$$

| Example No. | W | $R^1$ | X | m.p. (°C.) |
|---|---|---|---|---|
| 1. | t-butyl | —(CH$_2$)$_2$— | NHCO$_2$CH$_3$ | Oil |
| 2. | t-butyl | —(CH$_2$)$_2$— | NHCON(CH$_3$)$_2$ | 82–83 |
| 3. | t-butyl | —(CH$_2$)$_2$— | OCONHC$_6$H$_4$CF$_3$(4) | 152–155 |
| 4. | t-butyl | —(CH$_2$)$_2$— | NHCONHC$_6$H$_4$CF$_3$(4) | 128–130 |
| 5. | t-butyl | —(CH$_2$)$_2$— | OCOCH$_3$ | 110–112 |
| 6. | t-butyl | —(CH$_2$)$_2$— | NHCOCH$_2$Cl | 90–93 |
| 7. | t-butyl | —(CH$_2$)$_2$— | NHCONHCH$_3$ | 139–140 |
| 8. | t-butyl | —(CH$_2$)$_2$— | NHCOCHCH$_2$CH$_3$<br>\|<br>Cl | Oil |
| 9. | t-butyl | —(CH$_2$)$_2$— | NHCOC$_6$H$_5$ | 121–122 |
| 10. | t-butyl | —(CH$_2$)$_2$— | NHCOCH$_3$ | 100–102 |
| 11. | t-butyl | —(CH$_2$)$_2$— | NHCOCH$_2$CH$_2$Cl | 100–102 |
| 12. | t-butyl | —(CH$_2$)$_2$— | NHCOCHCH$_3$<br>\|<br>Cl | 90–92 |
| 13. | t-butyl | —(CH$_2$)$_2$— | NHCONHC$_6$H$_4$Cl(4) | 130–132 |
| 14. | t-butyl | —(CH$_2$)$_3$— | NHCON(CH$_3$)$_2$ | Oil |
| 15. | t-butyl | —(CH$_2$)$_2$— | NHCSNHC$_6$H$_4$Cl(4) | 150–151 |
| 16. | t-butyl | —(CH$_2$)$_2$— | NHCSNHCH$_3$ | gummy solid |

EXAMPLE A-Preparation of 3-t-butyl-5-thio-1H-1,2,4-triazole

To a suspension of thiosemicarbazide (500 g, 5.49 mole) in 2 liters of tetrahydrofuran (THF) in a 5 liter round bottomed flask cooled by an ice bath to 10° C. internal, was added trimethylacetyl chloride (694 grams (g), 5.76 mole) over thirty minutes. The exotherm was controlled to below 40° C. Then 482 g (6.04 mole) of 50 percent aqueous NaOH was added over thirty minutes with the exotherm controlled to below 50° C. The cooling bath was then removed and the mixture was stirred for two hours. Heat was then applied and 600 ml of THF was removed by distillation before starting the addition of a solution of 1500 ml of water and 835 g of 50 percent NaOH over ninety minutes. Removal of the THF was continued during this period until the internal temperature reached 80° C. The mixture was then refluxed an additional three hours and then cooled to room temperature before transferring into a 12 liter separatory funnel. Three kg of ice and 1500 ml of THF were added before the mixture was slowly acidified by 1500 ml of concentrated hydrochloric acid. The aqueous phase was separated and extracted with 2 liters of ethyl acetate before being discarded. The combined organic layers were washed with 2 liters of brine and dried over magnesium sulfate (500 g) and then concentrated in vacuo to afford 698 g of white solid 3-t-butyl-5-thio-1H-1,2,4-triazole, m.p. 205° C.

EXAMPLE B-Preparation of 3-t-butyl-5-(2-aminoethylthio)-1H-1,2,4-triazole dihydrobromide To 10 g (64 mmole) of 3-t-butyl-5-thio-1H-1,2,4-triazole suspended in 200 ml to ethyl acetate was a 13 g (64 mmole) of 2-bromoethylamine hydrobromide and the mixture was refluxed for eighteen hours. Evaporation of the ethyl acetate gave 23 g of the crude 3-t-butyl-5-(2-aminoethylthio)-1H-1,2,4-triazole dihydrobromide m.p. 252°-253° C. , which was sufficiently pure to be used in subsequent reactions.

Alternatively, to 77 g (438 mmole) of 3-t-butyl-5-thio-1,2,4-triazole suspended in 500 ml of THF was added 100 g (448 mmole) of 2-bromoethylamine hydrobromide and the mixture was refluxed for six hours. The reaction mixture was cooled and filtered to give 120 g of crude 3-t-butyl-5-(2-aminoethylthio)-1H-1,2,4-triazole dihydrobromide, (m.p. 252°-3° C. ) which was sufficiently pure to be used in subsequent reactions.

EXAMPLE C-Preparation of 3-t-butyl-5-(2-hydroxyethylthio)-1H-1,2,4-triazole

To 24 g (152 mmole) of 3-t-butyl-5-thio-1H-1,2,4-triazole suspended in 200 ml of ethyl acetate was added 20 g (152 mmole) of 2-bromoethanol. The resulting mixture was refluxed for eighteen hours. Upon cooling, 15.2 g (152 mmole) of triethylamine was added and the mixture was partitioned between ether and brine. The organic layer was dried over magnesium sulfate and concentrated in vacuo. The resulting oil was crystallized from ether/hexane to yield 25 g of 3-t-butyl-5-(2-hydroxyethylthio)-1H-1,2,4-triazole which was sufficiently pure to use in subsequent reactions.

EXAMPLE 1 -Preparation of 1-dimethylcarbamol-3-t-butyl-5-(2-(carbomethoxyamino)-ethylthio)-1H-1,2,4-triazole (Compound 1)

Step A

To 23 g of 3-t-butyl-5-(2-aminoethylthio)-1H-1,2,4-triazole dihydrobromide in 200 ml of tetrahydrofuran (THF) was added 19.5 g (193 mmole) of triethylamine and 6.6 g (70 mmole) of methyl chloroformate. After refluxing for three hours, the mixture was cooled and partitioned between ethyl acetate and water. The organic layer was dried (magnesium sulfate), filtered and evaporated to yield 13 g (39 mmole) of 3-t-butyl-5-(2-(carbomethoxyamino)-ethylthio)-1H-1,2,4-triazole which subsequent reaction without further purification.

Step B

To 13 g (39 mmole) of 3-t-butyl-5-(2-(carbomethoxyamino)-ethylthio)-1H-1,2,4-triazole was added 100 ml of THF, 0.5 g of 4-dimethylaminopyridine, 7 g (70 mmole) of triethylamine and 8 g (46 mmole) of dimethylcarbamoyl chloride. The mixture was refluxed for one hour and then partitioned between ether and water. The ether layer was separated and dried over magnesium sulfate, then filtered, concentrated in vacuo and chromatographed on silica gel (ethyl acetate/hexane). Three g of 1-dimethylcarbamoyl- 3-t-butyl-5-(2-(carbomethoxyamino)-ethylthio)-1H-1,2,4-triazole, an oil, was recovered.

EXAMPLE 2-Preparation of 1-dimethylcarbamoyl-3-t-butyl-5-(2-(4-trifluoromethylphenylcarbamoyloxy)-ethylthio)-1H-1,2,4-triazole (Compound 3)

To 5 g (20 mmole) of 3-t-butyl-5-(2-hydroxyethylthio)-1H-1,2,4-triazole in 50 ml of chloroform was added 0.1 g of triethylamine and 3.8 g (20 mmole) of 4-trifluoromethylphenylisocyanate. After refluxing for three hours, the mixture was concentrated in vacuo and crystallized from ether/hexane to give 3-t-butyl-5-(2-(4-trifluoromethylphenylcarbamoyloxy)-ethylthio)-1H-1,2,4-triazole.

3-t-Butyl-5-(2-(4-trifluoromethylphenylcarbamoyloxy)ethylthio)-1H-1,2,4-triazole was reacted by substantially the same method as Example 1, Step B, to yield 1-dimethyl-carbamoyl-3-t-butyl-5-(2-(4-trifluoromethylphenylcarbamoyloxy)-ethylthio)-1H-1,2,4-triazole, m.p. 152°-155° C.

EXAMPLE 3-Preparation of 1-dimethylcarbamoyl-3-t-butyl-5-(2-acetoxyethylthio)-1H-1,2,4-triazole (Compound 5)

To 10 g (64 mmole) of 3-t-butyl-5-thio-1H-1,2,4-triazole suspended in 150 ml of ethyl acetate was added 12 g (64 mmole) of 2-bromoethyl acetate and 12 (120 mmole) of triethylamine. The mixture was refluxed for eighteen hours, washed with brine, and dried over magnesium sulfate. The ethyl acetate was evaporated in vacuo and the residue was crystallized from ether/hexane to give 12 g of 3-t-butyl-5-(2-acetoxyethylthio)-1H-1,2,4-triazole, m.p. 114°-115° C.

The 3-t-butyl-5-(2-acetoxyethylthio)-1H-1,2,4-triazole was carbamoylated essentially by the procedure of Example 1, Step B, to yield 1-dimethylcarbamoyl-3-t-butyl-5-(2-acetoxyethylthio)-1H-1,2,4-triazole, m.p. 110°-112° C.

EXAMPLE 4-Preparation of 1-dimethylcarbamoyl-3-t-butyl-5-(2-(2-chlorobutanamido)-ethylthio)-1H-1,2,4-triazole (Compound 8)

3-t-Butyl-5-(2-(2-chlorobutanamido)-ethylthio)-1H-1,2,4-triazole, m.p. 68°-70° C. was prepared by substantially following the procedure of Example 1, Step A, and substituting 2-chlorobutyryl chloride for the methyl chloroformate.

1-Dimethylcarbamoyl-3-t-butyl-5-(2-(2-chlorobutanamido)-ethylthio)-1H-1,2,4-triazole, an oil, was prepared from 3-t-butyl-5-(2-(2-chlorobutanamido)-ethylthio)-1H-1,2,4-triazole by substantially following the procedure of Example 1, Step B.

The following compounds were made according to essentially the same procedure using the appropriate acid chloride:

1-Dimethylcarbamoyl-3-t-butyl-5-(2-(chloroacetamido)-ethylthio)-1H-1,2,4-triazole (Compound 6)

1-Dimethylcarbamoyl-3-t-butyl-5-(2-benzamido)-ethylthio)-1H-1,2,4-triazole (Compound 9).

1-Dimethylcarbamoyl-3-t-butyl-5-(2-acetamido)-ethylthio)-1H-1,2,4-triazole (Compound 10).

1-Dimethylcarbamoyl-3-t-butyl-5-(2-(3-chloropropanamido)-ethylthio)-1H-1,2,4-triazole (Compound 11).

1-Dimethylcarbamoyl-3-t-butyl-5-(2-(2-chloropropanamido)-ethylthio)-1H-1,2,4-triazole (Compound 12).

EXAMPLE 5-Preparation of
1-dimethylcarbamoyl-3-t-butyl
-5-(2-(4-trifluoromethylphenylcarbamoylamino)-ethylthio)-1H-1,2,4-triazole (Compound 4)

To 10 g (27 mmole) of 3-t-butyl-5-(2-aminoethylthio)-1H-1,2,4-triazole dihydrobromide in 100 ml of methylene chloride was added 5.5 g (54 mmole) of triethylamine. The mixture was cooled to −40° C. and a solution of 5.2 g (27 mmole) of 4-trifluoromethylphenyl isocyanate in methylene chloride was slowly added. The stirred mixture was slowly allowed to warm to room temperature and was stirred at room temperature for eighteen hours. The reaction mixture was washed twice with water, dried over magnesium sulfate, filtered and concentrated in vacuo to yield 9 g of 3-t-butyl-5-(2-(4-trifluoromethylphenylcarbamoylamino)-ethylthio)-1H-1,2,4-triazole, m.p. 238°–240° C.

3-t-Butyl-5-(2-(4-trifluoromethylphenylcarbamoylamino)-ethylthio)-1H-1,2,4-triazole was carbamoylated essentially by the procedure of Example 1, Step B, to yield 1-dimethylcarbamoyl-3-t-butyl-5-(2-(4-trifluoromethylphenylcarbamoylamino)-ethylthio)-1H-1,2,4-triazole.

The following compounds were made according to essentially the same procedure using the appropriate isocyanate or isothiocyanate:

1-Dimethylcarbamoyl-3-t-butyl-5-(2-methylcarbamoylamino)-ethylthio)-1H-1,2,4-triazole (Compound 7).

1-Dimethylcarbamoyl-3-t-butyl-5-(4-chlorophenylcarbamoylamino)-ethylthio)-1H-1,2,4-triazole (Compound 13).

1-Dimethylcarbamoyl-3-t-butyl-5-(2-(4-chlorophenyl thiocarbamoylamino)-ethylthio)-1H-1,2,4-triazole (Compound 15).

1-Dimethylcarbamoyl-3-t-butyl-5-(2-(methyl thiocarbamoylamino)-ethylthio)-1H-1,2,4-triazole (Compound 16).

EXAMPLE 6-Preparation of
1-dimethylcarbamoyl-3-t-butyl-5-(2-(dimethylcarbamoylamino)-ethylthio)-1H-1,2,4-triazole (Compound 2)

To 10 g (27 mmole) of 3-t-butyl-5-(2-aminoethylthio)-1H-1,2,4-triazole dihydrobromide in 50 ml of THF was added 0.5 g of 4-dimethylaminopyridine and 6 g (54 mmole) of dimethylcarbamoyl chloride and the mixture was stirred at room temperature for five minutes. Then 10 g of triethylamine was added dropwise and the mixture was refluxed for five minutes then stirred overnight at room temperature. Workup essentially as in Example 1, Step B, followed by crystallization from ether-hexane yielded 1-dimethylcarbamoyl-3-t-butyl-5-(2-(dimethylcarbamoylamino)-ethylthio)-1H-1,2,4-triazole, m.p. 82–83.

1-Dimethylcarbamoyl-3-t-butyl-5-(3-(dimethylcarbamoylamino)-propylthio)-1H-1,2,4-triazole (Compound 14) was made according to essentially the same procedure.

The compounds of the present invention have insecticidal activity. The activity of these compounds, especially towards aphids, allows for plant protection without disturbing beneficial insects, making these compounds especially useful in integrated pest management programs. Beneficial insects include pollinators, for example, bees; predators, for example, the lady beetles; and parasites, for example, wasps such as *Endovum puttlori*. In particular, the 1-dimethylcarbamoyl-3-substituted-5-substituted-1H-1,2,4-triazoles of the present invention show, for example, activity against Green Peach Aphids.

Accordingly, compounds of the present invention represent a genuine enrichment of the art.

On the basis of their initial insecticidal activity, compounds of the invention may be used in low dosages in controlling pests. The dosage depends on a variety of factors, for example, the compound used, the kind of pest, the formulation used, the state of the crop infected with the pest and the prevailing weather conditions. In general, for the control of pests in agriculture and horticulture, a dosage corresponding to from about 10 g to about 1000 g of the active compound per hectare may be used and from about 50 g to about 250 g per hectare of the active substance is preferred.

As previously noted, the compounds of the present invention are selective against sucking insects of the order Homoptera and especially those of the family Aphididea.

The compounds of the present invention, for practical applications, can be utilized in the form of compositions or formulations. In these compositions and formulations, the active substance is mixed with conventional inert (i.e., plant compatible and/or pesticidally inert) diluents or extenders such as solid carrier material or liquid carrier material, of the type usable in conventional compositions or formulations. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents.

The active compounds of the present invention may be employed alone or in the form of mixtures with one another and/or with such solid and/or liquid dispersible carrier vehicles and/or with other known compatible active agents, especially plant protection agents, such as other arthropodicides, nematocides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes and granules which are thus ready for use.

In the compositions of the present invention, the active compound is generally present in an amount substantially between about 0.0001 percent and 95 percent by weight. Mixtures suitable for direct application or field application generally contemplate those in which the active compound is present in an amount substantially between about 0.0001 percent and 5 percent, preferably between about 0.001 percent and 3 percent, by weight of the mixture. In ultra-low-volume applications, a liquid composition containing the active compound is usually applied as a spray (e.g., mist) by means of atomizing equipment in finely divided form (average particle size of from about 50 to about 100 microns or less) using airplane crop spraying techniques. Typically only a few liters per hectare are needed and often amounts up to about 15 to 1000 g/hectare, preferably about 40 to 600 g/hectare are sufficient. With ultra-low-volume, it is possible to use highly concentrated liquid compositions with said liquid carrier vehicles containing from about 20 to about 95 percent by weight of the active compound.

The present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, (e.g., a surface-active agent, such as an emulsifying agent and/or a dispersing agent), and an amount of the active compound which is effective for the purpose in question.

The active compounds can be applied as sprays by methods commonly employed, such as conventional high-gallonage hydraulic sprays, low gallonage sprays, ultra-low-volume sprays, airblast spray, aerial sprays and dusts.

Furthermore, the present invention contemplates methods of selectively killing, combating or controlling pests, which comprise applying to at least one of (a) such pests and (b) the corresponding habitat thereof (i.e., the locus to be protected, for example, to a growing crop or to an area where a crop is to be grown) a correspondingly combative or toxic amount (i.e., a pesticidally effective amount) of the particular active compound of the invention alone or together with a carrier vehicle as noted above.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases it is possible to go above or below the aforementioned concentration ranges.

The preparations according to the invention may also contain other substances commonly used in preparations of this kind. For example, a lubricant, such as calcium stearate or magnesium stearate, may be added to a wettable powder or to a mixture to be granulated. Furthermore there may be, for example, added "adhesives" such as polyvinyl alcohol cellulose derivatives or other colloidal materials, such as casein, to improve the adherence of the pesticide to the surface to be protected.

The compounds of the invention are also useful to control insects in seeds, generally by applying an effective amount of the compound to the surface area of the seeds to be treated. This may be accomplished by varying means common in the art, such as slurrying, soaking, dusting, spraying and the like.

Compositions and formulations according to the present invention may also include known pesticidal compounds. This expands the spectrum of activity of the preparations and may give rise to synergism.

The following known insecticidal, fungicidal and acaricidal compounds are suitable for use in such a combined preparation.

Insecticides such as:
1. Chlorinated hydrocarbons, for example, 2,2-bis(p-chlorophenyl)-1,1,1-trichloroethane and hexachloropoxyoctahydrodimethanonaphthalene.
2. Carbamates, for example, N-methyl-1-napththylcarbamate;
3. Dinitrophenols, for example, 2-methyl-4,6-dinitrophenyl and 2-(2-butyl)-4,6-dinitrophenyl-3,3-dimethylacrylate;
4. Organic phosphorus compounds, such as dimethyl-2-methoxy-carbonyl-1-methylvinyl phosphate, O,O-diethyl-O-p-nitrophenylphosphorus thioate; N-monomethylamide of O,O-dimethyldithiophosphoryl acetic acid;
5. Diphenylsulfides, for example, p-chlorobenzyl or p-chlorophenyl sulfide and 2,4,4'-5-tetrachloridiphenylsulfide;
6. Diphenylsulfonates, for example, p-chlorophenylbenzenesulfonate;
7. Methylcabinols, for example, 4,4-dichloro-1-trichloromethylbenzhydrol;
8. Quinoxaline compounds, such as methylquinoxaline dithiocarbonate;
9. Amidines such as N'-(4-chloro-O-tolyl)-N,N-dimethylformamidine;
10. Pyrethroids such as Allethrin;
11. Biologicals such as Bacillus thuringiensis preparations;
12. Organic tin compounds such as tricyclohexyltin hydroxide;

Fungicides such as:
13. Organic mercury compounds, for example, phenylmercuryacetate and methylmercurycyanoguanide;
14. Organic tin compounds, for example, triphenyltin hydroxide and triphenyltin acetate;
15. Alkylenebisdithiocarbamates, for example, zincethylenebisthiocarbamate and manganoethylenebisthiocarbamate; and furthermore
16. 2,4-Dinitro-6-(2-octyl-phenylcrotonate), 1-bis(-dimethylamino)phosphoryl-3-phenyl-5-amino-1,2-4-triazole, 6-methylquinoxaline-2,3-dithio-carbonate, 1,4-dithioantraquinone-2,3-dicarbonitrile, N-trichloromethylthiophthalimide, N-trichloromethylthiotetrahydrophthalimide, N-(1,1,2,2-tetrachloroethylthio)tetrahydrophthalimide, N-dichlorofluoromethylthio-N-phenyl-N'-dimethylsulfonyldiamide and tetrachloroisophthalonitrile.

Compounds according to the present invention were evaluated for their biological activity. In evaluating the foliar insecticidal activity of the compounds of this invention, the fcllowing test procedures were employed. A test solution containing 600 parts per million (ppm) was made by dissolving the test compound in a solvent (acetone:methanol, 1:1), adding a surfactant and then water to given an acetone:methanol:water system of 10:10:80. A 1:1 mixture of an alkylarylpolyetheralcohol (Triton ® X-155 surfactant from Rohm and Haas Company, Philadelphia, Pa.) and a modified phthalic glycerol alkyl resin (Triton ® B-1956 surfactant from Rohm and Haas Company, Philadelphia, Pa.) was utilized at the equivalent of 1 ounce per 100 gal. of test solution as a surfactant. Analogous solutions were made by serially diluting the 600 ppm test solution with water and surfactant to give concentrations of 150, 38, 10, 2.5, 0.6, 0.15 and 0.38 ppm. Not all compounds were tested at each of the several concentrations stated above. Test concentrations of a compound were selected as those most likely to differentiate dose response of a particular compound toward a particular test insect. Initial evaluations were made on one or more of the following pests:

| Code Symbol | Common Name | Latin Name |
|---|---|---|
| SAW | Southern Armyworm | *Spodoptera eridania* |
| MBB | Mexican Bean Beetle | *Epilachna varivestis* |
| GPA | Green Peach Aphid | *Myzus persicae* |
| TSM | Two-Spotted Spider Mite | *Tetranychus urticae* |
| BW | Boll Weevil | *Anthonomous grandis grandis* |

For the Mexican Bean Beetle and Southern Armyworm test, lima bean (*Phaseolus limensis* var. Woods' Prolific) seedlings in 3" pots were sprayed to run-off with the test solutions. When dry, each plant was placed in a plastic box (7.5" long×5.25" wide×3.75" deep). Each box was then infested with 10 third instar larvae of either the Mexican Been Beetle or the Southern Armyworm. The box was then sealed with a lid equipped with screened ventilation holes.

All treatments were maintained under continuous fluorescent light at 80° F. on open shelves for the course of the exposure period. Plants were watered as needed and replaced with untreated plants if they had been totally consumed as was the case with ineffective treatments or untreated checks or controls. Forty-eight hours after treatment, the percent mortality was determined for each test species and spray concentration.

For the mite test, infested bean (*Phaseolus limeanus*) leaf discs (1.25" diameter) containing about 50 mites were placed in a Petri dish lid on a moistened piece of cotton. The leaves were then sprayed to thorough wetness with the test solution using a rotating turntable, held for twenty-four hours and then the percentage killed was determined.

For the aphid test, infested broccoli (*Brassica oleracea italica*) leaves containing about 50 aphids were placed in a Petri dish lid on a moistened piece of cotton. The leaves were then sprayed to thorough wetness with the test solution using a rotating turntable, held for twenty-four hours and then the percentage killed was determined.

The mortalities obtained in this manner were plotted on logarithmic probability paper. The estimated concentration eliciting a 50 percent mortality ($LC_{50}$) was established from the best eye-fitted line to the plotted mortality data.

The results of the foliar insecticidal evaluations are given in Table II. Note the selectivity of certain compounds of this invention towards aphids.

TABLE II

| Example No. | Foliar Insecticidal Evaluations[1] Estimated $LC_{50}$ Values | | | | |
|---|---|---|---|---|---|
| | TSM | GPA | BB | AW | BW |
| 1 | >600 | 4 | 105 | 440 | 192 |
| 2 | 150 | 10 | 28 | 550 | >600 |
| 3 | 780 | 13 | 760 | >600 | 660 |
| 4 | >600 | 710 | >600 | >600 | >600 |
| 5 | >600 | 320 | >600 | >600 | >600 |
| 6 | >600 | 125 | >600 | >600 | >600 |
| 7 | >600 | 145 | 350 | >600 | >600 |

TABLE II-continued

| Example No. | Foliar Insecticidal Evaluations[1] Estimated $LC_{50}$ Values | | | | |
|---|---|---|---|---|---|
| | TSM | GPA | BB | AW | BW |
| 8 | >600 | 105 | 350 | >600 | >600 |
| 9 | >600 | >600 | 420 | >600 | >600 |
| 10 | >600 | 11 | 150 | >600 | 500 |
| 11 | >600 | 73 | 62 | >600 | >600 |
| 12 | >600 | 49 | 52 | >600 | >600 |
| 13 | >600 | >600 | 760 | >600 | >600 |
| 14 | >600 | 14 | 42 | >600 | 300 |
| 15 | 58 | 600 | 740 | >600 | >600 |
| 16 | 10 | 84 | 150 | >600 | >600 |

[1]Concentration in parts per million (ppm) which kills 50 percent of the stated insect.

It is to be understood that the present specification and examples are set forth by way of a illustration and not limitation and that various modifications and changes may be made without departing from the spirit and scope of the present invention as defined by the appended claims.

We claim:

1. A compound of the formula

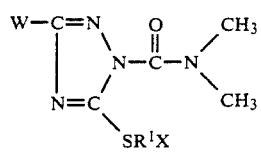

wherein
W is t-butyl, s-butyl, i-propyl, cyclopropyl, 1-methylthio-1-methylethyl or 1-methyl-cycloprop-1-yl;
X is

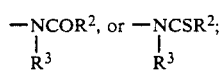

$R^1$ is unsubstituted or substituted —$(CH_2)_n$— having one to four of the same or different substituents independently selected from halo, cyano, nitro, —OR, —$CO_2R$, —OCOR, —COR, ($C_2$-$C_6$)alkenyl, ($C_2$-$C_6$)alkynyl, ($C_1$-$C_6$)alkyl, ($C_1$-$C_6$)haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —$CO_2R$, —COR, —OCOR, ($C_1$-$C_4$)alkyl, ($C_1$-$C_4$)alkoxy, ($C_1$-$C_4$)haloalkyl or ($C_2$-$C_6$)alkenyl;

each $R^2$ is independently hydrogen; unsubstituted or substituted ($C_1$-$C_8$)alkyl having one to three of the same or different substituents independently selected from halo, cyano, amino, nitro, —OR, —$CO_2R$, —COR or —OCOR; unsubstituted or substituted ($C_1$-$C_8$)alkoxy having one to three of the same or different substituents independently selected from halo, cyano, nitro, —OR, —$CO_2R$, —COR or —OCOR; unsubstituted or substituted ($C_1$-$C_{12}$)mono- or dialkylamino where the alkyl is substituted by one to three of the same or different substituents independently selected from halo, cyano, nitro, —OR, —$CO_2R$, —COR; unsubstituted or substituted ($C_6$-$C_{14}$)arylamino where the aryl is substituted by one to three of the same or different substituents independently selected from halo, cyano, nitro, trifluoromethoxy, difluoromethoxy, tetrafluoroethoxy, trifluoromethylthio, tetrafluoroethylthio, $-CO_2R$, $-COR$, $-OCOR$, $(C_1-C_4)$alkyl, $(C_1-C_4)$alkoxy, $(C_1-C_4)$-haloalkyl or $(C_2-C_6)$alkenyl; unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, $-CO_2R$, $-COR$, $-OCOR$, $(C_1-C_4)$alkyl, $(C_1-C_4)$ alkoxy, $(C_1-C_4)$haloalkyl or $(C_2-C_6)$alkenyl;

$R^3$ is hydrogen; unsubstituted or substituted $(C_1-C_6)$-alkyl having from one to four of the same or different substituents independently selected from halo, cyano, nitro, $-OR$, $-CO_2R$, $-OCOR$, $-COR$, $(C_2-C_6)$alkenyl, $(C_2-C_6)$alkynyl, $(C_1-C_6)$-alkyl, $(C_1-C_6)$haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, $-CO_2R$, $-COR$, $-OCOR$, $(C_1-C_4)$alkyl, $(C_1-C_4)$alkoxy, $(C_1-C_4)$haloalkyl or $(C_2-C_6)$alkenyl;

where each R is independently hydrogen; $(C_1-C_6)$alkyl; or phenyl optionally substituted with one to three of the same or different substituents independently selected from halo, cyano, nitro, hydroxy, trifluoromethoxy, difluoromethoxy, tetrafluoroethoxy, trifluoromethylthio, tetrafluoroethylthio, $(C_1-C_4)$alkyl, $(C_1-C_4)$alkoxy, $(C_1-C_4)$haloalkyl, $(C_2-C_6)$alkenyl, carboxy, $(C_1-C_4)$alkoxycarbonyl;

n is 1 to 10, and agronomically acceptable salts thereof.

2. The compound of claim 1 wherein
W is t-butyl;
X is $-NHCOR^2$, $-OC$ or $-NHCSR^2$;
$R^1$ is $-(CH_2)_n-$;
$R^2$ is unsubstituted or substituted $(C_1-C_8)$alkyl; unsubstituted or substituted $(C_1-C_8)$alkoxy; unsubstituted or substituted mono$(C_1-C_8)$aminoalkyl; unsubstituted or substituted di$(C_1-C_4)$-aminoalkyl; unsubstituted or substituted aminophenyl; where the substituent is halo, $(C_1-C_4)$haloalkyl, $(C_1-C_4)$alkoxy and $(C_1-C_4)$-thioalkoxy;
$R^3$ is hydrogen; and
n is 2 or 3; and agronomically acceptable salts thereof.

3. The compound of claim 2 wherein
$R^2$ is selected from the group consisting of $(C_1-C_8)$-alkyl; $(C_1-C_8)$haloalkyl; $(C_1-C_8)$alkoxy; $(C_1-C_8)$-monoalkylamino; $(C_1-C_8$(dialkylamino; phenyl; phenylamino; halophenylamino; and haloalkyl substibuted phenylamino.

4. The compound of claim 3 wherein
X is $NHCOR_2$.

5. The compound of claim 4 wherein
$R^2$ is selected from the group consisting of $(C_1-C_8)$monoalkylamino, $(C_1-C_8)$dialkylamino, phenylamino, and halosubstituted alkylphenylamino.

6. The compound of claim 4 wherein
$R^2$ is selected from the group consisting of $(C_1-C_8)$-alkyl, $(C_1-C_8)$haloalkyl and $(C_1-C_8)$alkoxy.

7. The compound of claim 3 wherien
X is $-NHCSR_2$.

8. The compound of claim 7 wherein
$R^2$ is selected from the group consisting of alkylamino, phenylamino, halophenylamino, and halosubstituted alkylphenylamino.

9. The compound of claim 3 wherein $R^1$ is $-(CH_2)_2-$; and
X is selected from the group consisting of $-NHCO_2CH_3$, $-NHCON(CH_3)_2$, $-NHCONHC_6H_4CF_3(4)$, $-NHCOCH_2Cl$, $-NHCONHCH_3$, $-NHCOCHClCH_2CH_3$, $-NHCOC_6H_5$, $-NHCOCH_3$, $-NHCOCH_2CH_2Cl$, $-NHCOCHClCH_3$, $-NHCONHC_6H_5Cl(4)$, $NHCSNHC_6H_4Cl(4)$ and $NHCSNHCH_3$.

10. The compound of claim 3 wherein
R is $-(CH_2)_3-$ and X is $NHCON(CH_3)_2$.

11. The compound of claim 3 wherein
R is $-(CH_2)_2-$ and X is $NHCON(CH_3)_2$.

12. The compound of claim 3 wherein
$R^1$ is $-(CH_2)_2-$ and X is $NHCO_2CH_3$.

13. The compound of claim 3 wherein
R is $-(CH_2)_2-$ and X is $NHCOCH_3$.

14. An insecticidal composition which comprises an agronomically acceptable carrier and an insecticidally effective amount of a compound of the formula $$\begin{array}{c} W-C=N \\ | \quad \quad \backslash \\ \quad \quad \quad N-C-N \\ | \quad \quad / \quad \overset{\overset{O}{\|}}{} \quad \backslash \\ N=C \quad \quad \quad \quad CH_3 \\ \quad \backslash \\ \quad SR^1X \end{array} \begin{array}{c} CH_3 \\ \\ CH_3 \end{array}$$

wherein
W is t-butyl, s-butyl, i-propyl, cyclopropyl, 1-methylthio-1-methylethyl or 1-methyl-cycloprop-1-yl;
X is $$-\underset{\underset{R^3}{|}}{N}COR^2, \text{ or } -\underset{\underset{R^3}{|}}{N}CSR^2;$$

$R^1$ is unsubstituted or substituted $-(CH_2)_n-$ having one to four of the same or different substituents independently selected from halo, cyano, nitro, $-OR$, $-CO_2R$, $-OCOR$, $-COR$, $(C_2-C_6)$alkenyl, $(C_2-C_6)$alkynyl, $(C_1-C_6)$alkyl, $(C_1-C_6)$haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, $-CO_2R$, $-COR$, $-OCOR$, $(C_1-C_4)$alkyl, $(C_1-C_4)$alkoxy, $(C_1-C_4)$haloalkyl or $(C_2-C_6)$alkenyl;

each $R^2$ is independently hydrogen; unsubstituted or substituted $(C_1-C_8)$alkyl having one to three of the same or different substituents independently selected from halo, cyano, amino, nitro, $-OR$, $-CO_2R$, $-COR$ or $-OCOR$; unsubstituted or substituted $(C_1-C_8)$alkoxy having one to three of the same or different substituents independently selected from halo, cyano, nitro, $-OR$, $-CO_2R$, $-COR$ or $-OCOR$; unsubstituted or substituted $(C_1-C_{12})$ mono- or dialkylamino where the alkyl is substituted by one to three of the same or different substituents independently selected from halo, cyano, nitro, $-OR$, $-CO_2R$, $-COR$; unsubstituted or substituted $(C_6-C_{14})$arylamino where the aryl is substituted by one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$)alkoxy, (C$_1$-C$_4$)-haloalkyl or (C$_2$-C$_6$)alkenyl; unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$) alkoxy, (C$_1$-C$_4$)haloalkyl or (C$_2$-C$_6$)alkenyl; R$^3$ is hydrogen; unsubstituted or substituted (C$_1$-C$_6$)-alkyl having from one to four of the same or different substituents independently selected from halo, cyano, nitro, —OR, —CO$_2$R, —OCOR, —COR, (C$_2$-C$_6$)alkenyl, (C$_2$-C$_6$)alkynyl, (C$_1$-C$_6$)alkyl, (C$_1$-C$_6$)haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$)alkoxy, (C$_1$-C$_4$)haloalkyl or (C$_2$-C$_6$)alkenyl;

where each R is independently hydrogen; (C$_1$-C$_6$)alkyl; or phenyl optionally substituted with one to three of the same or different substituents independently selected from halo, cyano, nitro, hydroxy, trifluoromethoxy, difluoromethoxy, tetrafluoromethoxy, trifluoromethylthio, tetrafluoroethylthio, (C$_1$-C$_4$)alkyl, (C$_1$-C$_4$)alkoxy, (C$_1$-C$_4$)haloalkyl, (C$_2$-C$_6$)alkenyl, carboxy, (C$_1$-C$_4$)alkoxycarbonyl;

n is 1 to 10; and agronomically acceptable salts thereof.

15. The composition of claim 14 wherein the compound is present at from about 0.0001 to about 99 percent by weight of the composition.

16. The composition of claim 15 wherein the compound is present from about 0.001 to about 90 percent by weight of the composition.

17. The composition of claim 16 wherein the compound is present from about 0.01 to about 75 percent by weight of the composition.

18. The composition of claim 14 wherein the agronomically acceptable carrier is a solid.

19. The composition of claim 14 wherein the agronomically acceptable carrier is a liquid.

20. A method of controlling insects which comprises contacting the insects with an insecticidally effective amount of a compound of the formula

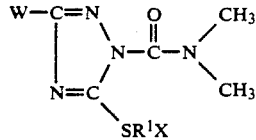

wherein

W is t-butyl, s-butyl, i-propyl, cyclopropyl, 1-methylthio-1-methylethyl or 1-methyl-cycloprop-1-yl;

X is

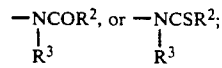

R$^1$ is unsubstituted or substituted —(CH$_2$)$_n$— having one to four of the same or different substituents independently selected from halo, cyano, nitro, —OR, —CO$_2$R, —OCOR, —COR, (C$_2$-C$_6$)alkenyl, (C$_2$-C$_6$)alkynyl, (C$_1$-C$_6$)alkyl, (C$_1$-C$_6$)haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$)alkoxy, (C$_1$-C$_4$)haloalkyl or (C$_2$-C$_6$)alkenyl;

each R$^2$ is independently hydrogen; unsubstituted or substituted (C$_1$-C$_8$)alkyl having one to three of the same or different substituents independently selected from halo, cyano, amino, nitro, —OR, —CO$_2$R, —COR or —OCOR; unsubstituted or substituted (C$_1$-C$_8$)alkoxy having one to three of the same or different substituents independently selected from halo, cyano, nitro, —OR, —CO$_2$R, —COR or —OCOR; unsubstituted or substituted (C$_1$-C$_{12}$)mono- or dialkylamino where the alkyl is substituted by one to three of the same or different substituents independently selected from halo, cyano, nitro, —OR, —CO$_2$R, —COR; unsubstituted or substituted (C$_6$-C$_{14}$)arylamino where the aryl is substituted by one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$)alkoxy, (C$_1$-C$_4$)-haloalkyl or (C$_2$-C$_6$)alkenyl; unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$) alkoxy, —C$_4$)haloalkyl or (C$_2$-C$_6$)alkenyl;

R$^3$ is hydrogen; unsubstituted or substituted (C$_1$-C$_6$)-alkyl having from one to four of the same or different substituents independently selected from halo, cyano, nitro, —OR, —CO$_2$R, —OCOR, —COR, (C$_2$-C$_6$)alkenyl, (C$_2$-C$_6$)alkynyl, (C$_1$-C$_6$)alkyl, (C$_1$-C$_6$)haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$-C$_4$)alkyl, (C$_1$-C$_4$)alkoxy, (C$_1$-C$_4$)haloalkyl or (C$_2$-C$_6$)alkenyl;

where each R is independently hydrogen; (C$_1$-C$_6$)alkyl; or phenyl optionally substituted with one to three of the same or different substituents independently selected from halo, cyano, nitro, hydroxy, trifluoromethoxy, difluoromethoxy, tetrafluoroethoxy, trifluoromethylthio, tetrafluoroethylthio, (C$_1$-C$_4$)alkyl, (C$_1$-C$_4$)alkoxy, (C$_1$-C$_4$)haloalkyl, (C$_2$-C$_6$)alkenyl, carboxy, (C$_1$-C$_4$)alkoxycarbonyl;

n is 1 to 10; and agronomically acceptable salts thereof.

21. A method of controlling aphids which comprises contacting the aphids with an aphidicidally effective amount of a compound of the formula

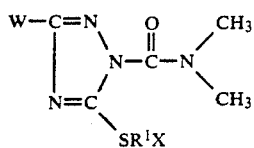

wherein

W is t-butyl, s-butyl, i-propyl, cyclopropyl, 1-methylthio-1-methylethyl or 1-methyl-cycloprop-1-yl;

X is

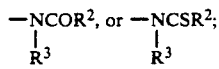

R$^1$ is unsubstituted or substituted —(CH$_2$)$_n$— having one to four of the same or different substituents independently selected from halo, cyano, nitro, —OR, —CO$_2$R, —OCOR, —COR, (C$_2$–C$_6$)alkenyl, (C$_2$–C$_6$)-alkynyl, (C$_1$–C$_6$)alkyl, (C$_1$–C$_6$)haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$–C$_4$)alkyl, (C$_1$–C$_4$)alkoxy, (C$_1$–C$_4$)haloalkyl or (C$_2$–C$_6$)alkenyl;

each R$^2$ is independently hydrogen; unsubstituted or substituted (C$_1$–C$_8$)alkyl having one to three of the same or different substituents independently selected from halo, cyano, amino, nitro, —OR, —CO$_2$R, —COR or —OCOR; unsubstituted or substituted (C$_1$–C$_8$)alkoxy having one to three of the same or different substituents independently selected from halo, cyano, nitro, —OR, —CO$_2$R, —COR or —OCOR; unsubstituted or substituted (C$_1$–C$_{12}$)mono- or dialkylamino where the alkyl is substituted by one to three of the same or different substituents independently selected from halo, cyano, nitro, —OR, —CO$_2$R, —COR; unsubstituted or substituted (C$_6$–C$_{14}$)arylamino where the aryl is substituted by one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$–C$_4$)alkyl, (C$_1$–C$_4$)alkoxy, (C$_1$–C$_4$)-haloalkyl or (C$_2$–C$_6$)alkenyl; unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, (C$_1$–C$_4$)alkyl, (C$_1$–C$_4$) alkoxy, (C$_1$–C$_4$)haloalkyl or (C$_2$–C$_6$)alkenyl; provided when X is NHCOR$^2$, R$^2$ is not unsubstituted phenyl or (4-chlorophenyl)amino;

R$^3$ is hydrogen; unsubstituted or substituted (C$_1$–C$_6$)alkyl having from one to four of the same or different substituents independently selected from halo, cyano, nitro, —OR, —CO$_2$R, —OCOR, —COR, (C$_2$–C$_6$)alkenyl, (C$_2$–C$_6$)alkynyl, (C$_1$–C$_6$)alkyl, (C$_1$–C$_6$)haloalkyl; or unsubstituted or substituted phenyl having one to three of the same or different substituents independently selected from halo, cyano, nitro, trifluoromethoxy, difluoromethoxy, tetrafluoroethoxy, trifluoromethylthio, tetrafluoroethylthio, —CO$_2$R, —COR, —OCOR, C$_1$–C$_4$)alkyl, (C$_1$–C$_4$)alkoxy, (C$_1$–C$_4$)haloalkyl or (C$_2$–C$_6$)alkenyl; provided when X is NHCOR$^2$, R$^2$ is not unsubstituted phenyl or (4-chlorphenyl)amino;

where each R is independently hydrogen; (C$_1$–C$_6$)alkyl; or phenyl optionally substituted with one to three of the same or different substituents independently selected from halo, cyano, nitro, hydroxy, trifluoromethoxy, difluoromethoxy, tetrafluoroethoxy, trifluoromethylthio, tetrafluoroethylthio, (C$_1$–C$_4$)alkyl, (C$_1$–C$_4$)alkoxy, (C$_1$–C$_4$)haloalkyl, (C$_2$–C$_6$)alkenyl, carboxy, (C$_1$–C$_4$)alkoxycarbonyl; and n is 1 to 10; and agronomically acceptable salts thereof.

22. The method of claim 21 wherein the compound is applied at from about 10 g to about 5000 g per hectare.

23. The method of claim 22 wherein the compound is applied at from about 50 g to about 2500 g per hectare.

24. The method of claim 20 wherein the compound is applied at from about 10 g to about 5000 g per hectare.

25. The method of claim 24 wherein the compound is applied at from about 50 g to about 2500 g per hectare.

* * * * *